United States Patent
Nair et al.

(10) Patent No.: US 9,029,616 B2
(45) Date of Patent: May 12, 2015

(54) PROCESS FOR 1-CHLORO-3,3,3-TRIFLUOROPROPENE FROM TRIFLUOROMETHANE

(71) Applicant: Honeywell International Inc., Morristown, NJ (US)

(72) Inventors: Haridasan K. Nair, Williamsville, NY (US); Andrew Joseph Poss, Kenmore, NY (US); David Nalewajek, West Seneca, NY (US); Yian Zhai, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/330,659

(22) Filed: Jul. 14, 2014

(65) Prior Publication Data

US 2015/0045588 A1 Feb. 12, 2015

Related U.S. Application Data

(60) Provisional application No. 61/863,725, filed on Aug. 8, 2013.

(51) Int. Cl.
| | | |
|---|---|---|
| C07C 17/25 | (2006.01) | |
| C07C 17/281 | (2006.01) | |
| C07C 17/10 | (2006.01) | |
| C07C 17/275 | (2006.01) | |
| C07C 17/278 | (2006.01) | |

(52) U.S. Cl.
CPC .............. *C07C 17/25* (2013.01); *C07C 17/281* (2013.01); *C07C 17/10* (2013.01); *C07C 17/275* (2013.01); *C07C 17/278* (2013.01)

(58) Field of Classification Search
CPC ...... C07C 17/25; C07C 17/10; C07C 17/278; C07C 17/275; C07C 17/281
USPC .................................................. 570/155, 159
See application file for complete search history.

(56) References Cited

U.S. PATENT DOCUMENTS

| | | |
|---|---|---|
| 5,777,184 A | 7/1998 | Van Der Puy et al. |
| 6,472,573 B1 | 10/2002 | Yamamoto et al. |
| 6,958,424 B1 * | 10/2005 | Nair et al. ................ 570/261 |
| 8,754,272 B2 * | 6/2014 | Zhai et al. ................ 570/156 |
| 2005/0033097 A1 | 2/2005 | Tung et al. |
| 2009/0270661 A1 | 10/2009 | Wang et al. |
| 2011/0031436 A1 | 2/2011 | Mahler et al. |
| 2011/0083955 A1 | 4/2011 | Tirtowidjojo et al. |
| 2011/0172470 A1 | 7/2011 | Hamasaki et al. |
| 2011/0201853 A1 | 8/2011 | Tung et al. |
| 2011/0218370 A1 | 9/2011 | Elsheikh et al. |
| 2012/0271069 A1 | 10/2012 | Wang et al. |

FOREIGN PATENT DOCUMENTS

| | | |
|---|---|---|
| EP | 2327680 | 6/2011 |
| WO | 2009137658 A2 | 5/2008 |
| WO | 2008054781 A1 | 11/2009 |
| WO | 2013085765 A1 | 6/2013 |

* cited by examiner

*Primary Examiner* — Shailendra Kumar
(74) *Attorney, Agent, or Firm* — Erika Wilson

(57) ABSTRACT

The present invention provides routes for making 1-chloro-3,3,3-trifluoropropene (HCFO-1233zd) from commercially available raw materials. More specifically, this invention provides routes for HCFO-1233zd from inexpensive and commercially available trifluoromethane (HFC-23).

12 Claims, No Drawings

PROCESS FOR 1-CHLORO-3,3,3-TRIFLUOROPROPENE FROM TRIFLUOROMETHANE

CROSS-REFERENCE TO RELATED APPLICATION

This application claims priority from commonly owned U.S. Provisional Application Ser. No. 61/863,725 filed 8 Aug. 2013, the disclosure of which is hereby incorporated herein by reference.

FIELD OF THE INVENTION

The present invention provides routes for making 1-chloro-3,3,3-trifluoropropene (HCFO-1233zd) from commercially available raw materials. More specifically, this invention provides routes for HCFO-1233zd from inexpensive and commercially available fluoroform, i.e., trifluoromethane (HFC-23).

BACKGROUND OF THE INVENTION

Trans 1-chloro-3,3,3-trifluoropropene (HCFO-1233zd) can be used for many applications including use as a refrigerant, blowing agent, solvent, cleaning agent and monomer for polymer compounds. The compounds of the present invention are part of a continued search for the next generation low global warming potential materials with low environmental impact.

Many methods are known in the art for making HCFO-1233zd (trans), most of them using three carbon starting materials which are obtained in multiple steps. For example, U.S. Pat. Nos. 5,777,184 and 6,472,573 describe the preparation of $CF_3CH=CHCl$ from $CCl_3CH_2CHCl_2$ (240fa) with HF in the presence of a catalyst. Treatment of $CF_3CH_2CF_2H$ (245fa) with hydrogen chloride at 280° C. with chromium catalyst is reported to give 1233zd (trans and cis), see EP 2327680. Reaction of $CF_3CH=CH_2$ with chlorine and HF affords 1233zd as one of the products (WO 2008/54782 A1).

All of the above processes involve three carbon starting materials which in turn are made in multiple steps and thus there is a need to develop cost effective routes which utilize commercially available raw materials. The present invention addresses this issue by utilizing fluoroform, $CF_3H$ (HFC-23).

SUMMARY OF THE INVENTION

The present invention describes the preparation of HCFO-1233zd from commercially available fluoroform, (trifluoromethane, $CF_3H$, HFC-23). HFC-23 is a side product in the manufacture of Teflon® and is commercially available in large quantities. The compound ($CF_3H$) is both inexpensive and non-toxic, making it an excellent starting material for the formation of HCFO-1233zd. In many industrial operations, HFC-23 is discarded by burning and the utilization of this waste material for the formation of useful compounds is highly desirable for reducing this environmental impact.

HFC-23 can be converted to $CF_3Cl$ with chlorine which can then be added to chloro- or dichloro-ethylene compounds such as $CHCl=CHCl$, $CH_2=CHCl$, $CH_2=CCl_2$ to afford appropriate three carbon synthons from which 1233zd can be obtained by either dehalogenation or dehydrochlorination. These reactions can be conducted in either the liquid phase or the gas phase, as depicted in reaction Schemes 1A-C, shown below:

Scheme 1:

A

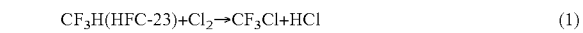

(1)

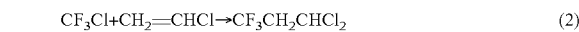

(2)

(3)

B

(4)

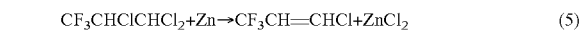

(5)

C

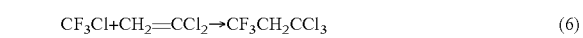

(6)

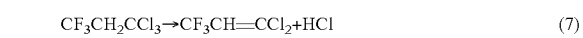

(7)

(8)

(9)

In Scheme 1B the addition of $CF_3Cl$ to 1,2-dichloroethylene is followed by Zn mediated dechlorination to afford HCFO-1233zd. In Scheme 1C, addition of chlorotrifluoromethane to 1,1-dichloroethylene is followed by dehydrochlorination, and hydrogenation and dehydrohalogenation to afford $CF_3CH=CHCl$.

This starting material may generically be depicted as $CHX=CYZ$, where $X=H$ or $Cl$, $Y=H$ or $Cl$, and $Z=H$ or $Cl$.

Also, $CH_2=CH_2$ can be used instead of the above chloroethylenes to give $CF_3CH_2CH_2Cl$ which can be selectively chlorinated to $CF_3CH_2CHCl_2$ and dehydrochlorinated to give HCFO-1233zd, as follows:

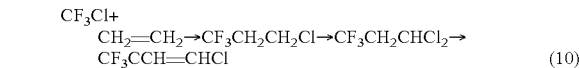

(10)

Fluoroform ($CF_3H$) can also be converted directly into HCFO-1233zd when reacted with an appropriate catalyst at an elevated temperature. For example, when a mixture $CF_3H$ and 1,2-dichloroethylene (trans/cis) is passed over a catalyst such as Cu/CuI impregnated activated carbon catalyst, the product $CF_3CH=CHCl$ (HCFO-1233zd) was obtained, as depicted in the following reaction scheme.

Scheme 2:

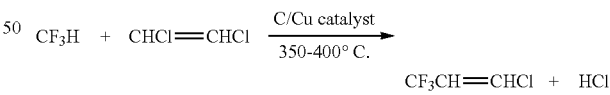

The C/Cu catalyst is made by impregnating nanocopper particles on activated carbon pellets or granular carbon. Copper nanoparticles were impregnated on activated carbon by refluxing CuI in absolute ethanol and appropriate carbon (pellet/granular); the resultant Cu-impregnated carbon is decanted, washed with ethanol and dried for 12 hours at 100° to 200° C. prior to use.

It should be appreciated by those persons having ordinary skill in the art(s) to which the present invention relates that any of the features described herein in respect of any particular aspect and/or embodiment of the present invention can be combined with one or more of any of the other features of any other aspects and/or embodiments of the present invention described herein, with modifications as appropriate to ensure compatibility of the combinations. Such combinations are considered to be part of the present invention contemplated by this disclosure.

It is to be understood that both the foregoing general description and the following detailed description are exemplary and explanatory only and are not restrictive of the invention as claimed. Other embodiments will be apparent to those skilled in the art from consideration of the specification and practice of the invention disclosed herein.

DETAILED DESCRIPTION OF THE INVENTION

As set forth above, the present invention provides synthetic routes for making 1-chloro-3,3,3-trifluoroprop ene (HCFO-1233 zd) from an inexpensive and commercially available compound, trifluoromethane (HFC-23).

Accordingly, one embodiment of the invention is directed to a process for the formation of 1-chloro-3,3,3-trifluoropropene from $CF_3H$(HFC-23) selected from the group of reactions consisting of:
  (a) the catalytic reaction of 1,2-dichloroethylene with $CF_3H$ at a temperature of from 350° to 400° C.;
  (b) a reaction comprising the steps of:
    (i) the chlorination of $CF_3H$ to form $CF_3Cl$;
    (ii) the reaction of $CF_3Cl$ with one or more chloroethylene compounds to form one or more chlorofluorocarbon three carbon synthon compounds; and
    (iii) the conversion of the three carbon synthon compounds to $CF_3CH=CHCl$; and
  (c) a combination of reactions (a) and (b).

In certain embodiments, the chloroethylene compounds are selected from the group consisting of 1-chloroethylene, 1,1-dichloroethylene and 1,2-dichloroethylene and mixtures of two or more.

In certain embodiments, the chloroethylene compound comprises 1-chloroethylene.

In certain embodiments, the chloroethylene compound comprises 1,1-dichloroethylene.

In certain embodiments, the chloroethylene compound comprises 1,2-dichloroethylene.

In certain embodiments, the three carbon synthon compounds are selected from the group consisting of 1,1-dichloro-3,3,3-trifluoropropane, 1,1-dichloro-2-chloro-3,3,3-trifluoropropane, 1,1,1-trichloro-3,3,3-trifluoropropane, and mixtures of two or more of these compounds.

In certain embodiments the three carbon synthon compound comprises 1,1-dichloro-3,3,3-trifluoropropane.

In certain embodiments the three carbon synthon compound comprises 1,1-dichloro-2-chloro-3,3,3-trifluoropropane.

In certain embodiments the three carbon synthon compound comprises 1,1,1-trichloro-3,3,3-trifluoropropane.

Another embodiment of the invention is directed to a process for the formation of 1-chloro-3,3,3-trifluoropropene comprising the catalytic reaction of 1,2-dichloroethylene with $CF_3H$ at a temperature of from 350° to 400° C.

Yet another embodiment of the invention is directed to a process for the formation of 1-chloro-3,3,3-trifluoropropene from $CF_3H$(HFC-23) comprising the steps of:
  (a) the chlorination of $CF_3H$ to form $CF_3Cl$;
  (b) the reaction of $CF_3Cl$ with one or more chloroethylene compounds to form one or more chlorofluorocarbon three carbon synthon compounds; and
  (c) the conversion of the three carbon synthon compounds to $CF_3CH=CHCl$.

In certain embodiments the chloroethylene compounds are selected from the group consisting of 1-chloroethylene, 1,1-dichloroethylene and 1,2-dichloroethylene, and mixtures of two or more.

In certain embodiments, the chloroethylene compound comprises 1-chloroethylene.

In certain embodiments, the chloroethylene compound comprises 1,1-dichloroethylene.

In certain embodiments, the chloroethylene compound comprises 1,2-dichloroethylene.

In certain embodiments, the three carbon synthon compounds are selected from the group consisting of 1,1-dichloro-3,3,3-trifluoropropane, 1,1,2-trichloro-3,3,3-trifluoropropane, 1,1,1-trichloro-3,3,3-trifluoropropane, and mixtures of two or more.

In certain embodiments, the three carbon synthon compound comprises 1,1-dichloro-3,3,3-trifluoropropane.

In certain embodiments, the three carbon synthon compound comprises 1,1,2-trichloro-3,3,3-trifluoropropane.

In certain embodiments, the three carbon synthon compound comprises 1,1,1-trichloro-3,3,3-trifluoropropane.

In general, it is possible that certain reactions employed herein can be carried out in the liquid or in the gas phase, or in a combination of gas and liquid phases, and it is contemplated that the reactions can be carried out batch wise, continuous, or a combination of these.

Preferably the reactor vessel is comprised of materials which are resistant to corrosion as Hastelloy, Inconel, Monel and/or fluoropolymers linings.

In certain embodiments, the reactor vessel contains catalyst, for example a fixed or fluid catalyst bed, packed with a suitable catalyst, with suitable means to ensure that the reaction mixture is maintained with the desired reaction temperature range.

In general it is also contemplated that a wide variety of reaction pressures may be used for the reactions, depending again on relevant factors such as the specific catalyst being used. The reaction pressure can be, for example, superatmospheric, atmospheric or under vacuum and in certain preferred embodiments is from about 1 to about 200 psia, and in certain embodiments from about 1 to about 120 psia.

In certain embodiments, an inert diluent gas, such as nitrogen, may be used in combination with the other reactor feed(s).

It is contemplated that the amount of catalyst use will vary depending on the particular parameters present in each embodiment.

The following examples provide additional details regarding various embodiments of the present invention. However, the present invention is not limited to the following examples.

EXAMPLES

Example 1

Reaction of $CF_3H$ with $CHCl=CHCl$

Catalyst Preparation:
Activated carbon (Shirasagai or Aldrich) was refluxed with 5 M nitric acid (in the ratio 1 g/25 mL) for 4 hours, decanted, washed with de-ionized water until the pH of the washing became 7.0 and was then dried under vacuum for 12 hours. Then activated carbon with copper iodide in absolute ethanol (ratio of activated C:CuI:Ethanol=1:0.1:30) was refluxed for 4 hours, washed with 4×30 mL ethanol and dried at 110° C. for overnight prior to use.

A stainless steel tube (0.5 inch×14 inches) was loaded with 25 cc catalyst (Activated Shirasagai Carbon pellet impregnated with Cu/CuI nanoparticles) and heated to and maintained at 200° C. under a nitrogen purge (20 sccm). Then the temperature was raised to 350° C. and a mixture of $CF_3H$ and $CHCl=CHCl$ was passed over it with a contact time of from 10 to 60 seconds. The exit stream from the reactor was analyzed by GC and GC-MS. The percentage of $CF_3CH=CHCl$ in the exit stream ranged from 20% to 30%.

Example 2

Conversion of $CF_3H$ to $CF_3Cl$

A Monel tube reactor (0.5 inch×14 inches) was packed with 25 cm$^3$ activated carbon (granular, 4-14 mesh) and purged with nitrogen at 150° to 200° C. for one hour. The tube reactor was heated to and maintained at 300° C. and a mixture of $CF_3H$(HFC-23) and chlorine (in the ratio 1:3) was passed through the reactor in such way that the contact time was between 15 to 20 seconds. The product mixture in the exit stream was passed through a 10% aq. KOH solution and over $CaSO_4$ column; $CF_3Cl$ (HFC-13) was collected in a cylinder cooled by liquid nitrogen.

Typical yields ranged from 80% to 90%. The chlorination of $CF_3H$ was also done with other types of activated carbon such as Calgon or Shirasagai granular to give the $CF_3Cl$.

Example 3

Addition of $CF_3Cl$ to $CH_2=CHCl$

Into a 350 mL capacity Hastelloy C autoclave awes added ferric chloride (1.0 g), iron powder (0.2 g) and tributylphosphate (2.75 g). The autoclave was then purged with nitrogen, and pressurized/charged with $CF_3Cl$ (2.57 mol, 267 g) and then heated to a temperature of from 115° to 120° C. Then vinyl chloride was charged intermittently into the autoclave with constant stirring; as the addition takes place the pressure decreases and more $CH_2=CHCl$ was fed into the reactor. Total amount added was 167 g (2.7 mol). The product $CF_3CH_2CHCl_2$ was separated and distilled to afford 350 g (yield=82%).

Example 4

Addition of $CF_3Cl$ to $CHCl=CHCl$

This reaction was conducted exactly the same manner as in Example 3 except for the fact that $CH_2=CHCl$ was substituted by 1,2-dichloroethylene (trans/cis) $CHCl=CHCl$. The yield of $CF_3CHClCHCl_2$ ranged from 50% to 70%.

Example 5

This reaction was conducted exactly in the same manner as Example 3, except that $CH_2=CHCl$ was substituted by 1,1-dichloroethylene $CH_2=CCl_2$ or $CH_2=CH_2$ to afford 65% $CF_3CH_2CCl_3$ or $CF_3CH_2CH_2Cl$ (60%), respectively Example 6

Conversion of $CF_3CH_2CHCl_2$ to $CF_3CH=CHCl$ (HCFO-1233zd)

Step (A)

Liquid Phase

To a 25% aq. KOH solution containing 2% Aliquat 336 by weight was heated to and maintained at 40° C. $CF_3CH_2CHCl_2$ was added drop-wise over a period of 1 hour; the product was collected in cold trap (−78° C., dry ice/IPA). The molar ratio of KOH to $CF_3CH_2CHCl_2$ was 1:1 equivalent. The yields of HCFO-1233zd ranged from 80% to 90%.

Step (B)

Vapor Phase

A stainless steel tubular reactor was charged with 25 cc fluorinated $Cr_2O_3$ catalyst. Then the reactor tube was heated under purge of nitrogen to 400° C. Nitrogen flow was stopped and $CF_3CHCHCl_2$ was fed at a flow rate of from 0.2 to 0.5 cc/min which was fed to a vaporizer and then to the tubular reactor; the exit stream contained mainly HCFO-1233zd, at a yield greater than 80%, in addition to some unreacted starting material.

Example 7

Conversion $CF_3CH_2CCl_3$ to $CF_3CH=CCl_2$

This reaction was conducted essentially the same manner as described in Example 6 in liquid and vapor phases; the yields ranged between 50-70%.

Example 8

Hydrogenation of $CF_3CH=CCl_2$ to $CF_3CH_2CHCl_2$

Into a 1 L stainless steel autoclave was added 1 g of hydrogenation catalyst (about 2% Pd on C), and 200 mL methanol under a nitrogen purge. The autoclave was sealed, cooled to −20° C. and evacuated to remove excess nitrogen; then 0.40 mol of $CF_3CH=CCl_2$ was added. Then autoclave was brought to about 0° C. and slowly charged with 0.4 mol $H_2$; the reaction mixture was stirred continuously and the pressure drop was monitored over time. The reaction was stopped once there was no pressure change over a period of 1 hour. The product, mainly $CF_3CH_2CHCl_2$, was distilled off from the reactor (0.30 mol, 75% yield).

Example 9

Conversion of $CF_3CHClCHCl_2$ to $CF_3CH=CHCl$

To a stirred mixture of Zn powder (activated with acetic acid/acetic anhydride) (14.4 g, 0.21 mol) and dry methanol (25 mL) was added $CF_3CHClCH_2Cl$ (0.10 mol) drop-wise with an addition funnel at from 50° to 55° C. over a period of 2 hours. The volatile material formed from the reaction was collected in a cold trap to afford 60% yield of $CF_3CH=CHCl$.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

It should be understood that the foregoing description is only illustrative of the present invention. Various alternatives and modifications can be devised by those skilled in the art without departing from the invention. Accordingly, the present invention is intended to embrace all such alternatives, modifications and variances that fall within the scope of the appended claims.

What is claimed is:

1. A process for the formation of 1-chloro-3,3,3-trifluoropropene from $CF_3H$ (HFC-23) comprising the catalytic reaction of 1,2-dichloroethylene with $CF_3H$ at a temperature of from 350° C. to 400° C.

2. A process for the formation of 1-chloro-3,3,3-trifluoropropene from $CF_3H$ (HFC-23) comprising the steps of:
   (i) the chlorination of $CF_3H$ to form $CF_3Cl$;
   (ii) the reaction of $CF_3Cl$ with one or more chloroethylene compounds to form one or more chlorofluorocarbon three carbon synthon compounds; and
   (iii) the conversion of the three carbon synthon compounds to $CF_3CH=CHCl$.

3. The process of claim 2, wherein the chloroethylene compounds are selected from the group consisting of 1-chloroethylene, 1,1-dichloroethylene and 1,2-dichloroethylene and mixtures of two or more.

4. The process of claim 2, wherein the chloroethylene compound comprises 1-chloroethylene.

5. The process of claim 2, wherein the chloroethylene compound comprises 1,1-dichloroethylene.

6. The process of claim 2, wherein the chloroethylene compound comprises 1,2-dichloroethylene.

7. The process of claim 2, wherein the three carbon synthon compounds are selected from the group consisting of 1,1-dichloro-3,3,3-trifluoropropane, 1,1-dichloro-2-chloro-3,3,3-trifluoropropane, 1,1,1-trichloro-3,3,3-trifluoropropane, and mixtures of two or more.

8. The process of claim 2, wherein the three carbon synthon compound comprises 1,1-dichloro-3,3,3-trifluoropropane.

9. The process of claim 2, wherein the three carbon synthon compound comprises 1,1-dichloro-2-chloro-3,3,3-trifluoropropane.

10. The process of claim 2, wherein the three carbon synthon compound comprises 1,1,1-trichloro-3,3,3-trifluoropropane.

11. A process for the formation of 2-chloro-3,3,3-trifluoropropene comprising the catalytic reaction of 1,2-dichloroethylene with $CF_3H$ at a temperature of from 350° to 400° C.

12. A process for the formation of 1-chloro-3,3,3-trifluoropropene from $CF_3H$ (HFC-23) comprising the steps of:
   (i) the chlorination of $CF_3H$ to form $CF_3Cl$;
   (ii) the reaction of $CF_3Cl$ with $CH_2=CH_2$ to form the compound $CF_3CH_2CH_2Cl$;
   (iii) the selective chlorination of $CF_3CH_2CH_2Cl$ to form the compound $CF_3CH_2CHCl_2$; and
   (iv) the dehydrochlorination of $CF_3CH_2CHCl_2$ into $CF_3CH=CHCl$.

* * * * *